United States Patent [19]

Oulman et al.

[11] 4,277,635

[45] Jul. 7, 1981

[54] PROCESS OF CONCENTRATING ETHANOL FROM DILUTE AQUEOUS SOLUTIONS THEREOF

[75] Inventors: Charles S. Oulman, Ames; Colin D. Chriswell, Slater, both of Iowa

[73] Assignee: Iowa State University Research Foundation, Inc., Ames, Iowa

[21] Appl. No.: 162,524

[22] Filed: Jun. 24, 1980

[51] Int. Cl.$^3$ .................... C07C 31/08; C07C 29/76
[52] U.S. Cl. .................................. 568/916; 568/917
[58] Field of Search ............................... 568/916, 917

[56] References Cited

U.S. PATENT DOCUMENTS

| | | | |
|---|---|---|---|
| 1,985,204 | 12/1934 | Derr et al. | 568/917 |
| 1,985,205 | 12/1934 | Derr | 568/917 |
| 2,564,717 | 8/1951 | Olsen | 568/917 |
| 2,619,497 | 11/1952 | Hockberger | 568/917 |
| 3,485,879 | 12/1969 | Mameniskis et al. | 568/917 |
| 4,061,724 | 12/1977 | Grose et al. | 423/339 |
| 4,073,865 | 2/1978 | Flanigen et al. | 423/339 |

OTHER PUBLICATIONS

Flanigen et al., "Nature", vol. 271, 9 Feb. 1978, pp. 512–516.

*Primary Examiner*—Joseph E. Evans

[57] ABSTRACT

Relatively dilute aqueous solutions of ethanol are concentrated by passage through a bed of a crystalline silica polymorph, such as silicalite, to adsorb the ethanol with residual dilute feed in contact with the bed, which is displaced by passing concentrated aqueous ethanol through the bed without displacing the adsorbed ethanol. A product concentrate is then obtained by removing the adsorbed ethanol from the bed together with at least a portion of the concentrated aqueous ethanol used as the displacer liquid. This process permits ethanol to be concentrated from dilute fermentation beers, which may contain from 6 to 10% ethanol, to obtain a concentrate product at very low energy cost having an ethanol concentration in excess of 95%, such as a concentration of from 98 to 99.5%.

11 Claims, 5 Drawing Figures

PROCESS OF CONCENTRATING ETHANOL FROM DILUTE AQUEOUS SOLUTIONS THEREOF

CONTRACT REFERENCE

This invention was made in part under Department of Energy Contract No. W-7405-ENG-82.

BACKGROUND AND PRIOR ART

The general field of this invention relates to processes for concentrating ethanol from aqueous solutions thereof, such as fermentation beer, to obtain an ethanol concentrate which can be used as a motor fuel, or mixed with gasoline to produce a motor fuel, such as gasohol. More specifically, the field of this invention relates to adsorption processes for concentrating ethanol from aqueous solutions thereof.

Ethanol can be readily produced by fermentation processes, which yield dilute aqueous solutions of ethanol. However, the concentration of ethanol from aqueous solutions by the traditional distillation processes used for producing beverage grade ethyl alcohol requires large amounts of heat energy. Beverage grade ethyl alcohol is usually produced as the azeotrope containing about 5% water by weight. It has been estimated that the production of this azeotrope by distillation requires about 1.4 to 1.6 times more energy than will be liberated when the ethanol is burned as a fuel. The cost of growing and gathering the biomass for the fermentation is additional, and this cost is higher where an expensive cereal grain is used such as corn. Further, for some motor fuel uses, such as in producing gasohol, the ethanol must be substantially anhydrous, and therefore a further azeotropic distillation requires as much energy as the fuel value of the alcohol. See Hartline, "Lowering the Cost of Alcohol", *Science,* Vol. 206, 41-42 (1979).

The Hartline article cited above reviews various attempts to develop lower cost processes for concentrating ethanol from fermentation beers. The only adsorption process mentioned in this article refers to experiments with the use of zeolites as molecular sieves to selectively adsorb water from aqueous ethanol, thereby increasing the concentration of the residual solution. It is stated that a promising candidate for such a process is clinoptilolite, which is a naturally occurring zeolite, and the article also referred to tests with synthetic zeolites for the same purpose being conducted by the Linde Division of Union Carbide Corporation.

It is known that silicalite and similar crystalline silica polymorphs are capable of removing small molecule organic compounds from dilute aqueous solutions, such as wastewater contaminated with organics, which need to be removed to reduce the BOD of the water. See U.S. Pat. Nos. 4,061,724 and 4,073,865, and Flanigen et al, "Silicalite A New Hydrophobic Crystalline Silica Molecular Sieve" *Nature,* Vol. 271, pp 512-516, (1978). Although silicalite is commercially available from the Linde Division of Union Carbide Corporation, prior to the present invention its use has not been suggested for concentrating ethanol in fermentation beer to obtain a highly concentrated ethanol product.

SUMMARY OF INVENTION

The present invention provides a practical and efficient low energy process for concentrating ethanol from aqueous solutions thereof, such as fermentation beer containing from 6 to 10% by weight ethanol. The ethanol was removed from the fermentation beer or other aqueous solution of ethanol by adsorption on a crystalline silica polymorph such as silicalite. Although it was known that lower alcohols and other small molecule organic compounds can be removed from water by contacting the water with silicalite, as far as is known, silicalite had not heretofore been used as a basis of a process for producing ethanol or other organic compound in high concentrations.

When ethanol is being removed from a dilute aqueous solution thereof by adsorption on silicalite, the bed of silicalite or column containing the silicalite adsorbent remained filled with the dilute fermentation beer or other aqueous solution of ethanol being processed. The residual fermentation beer will therefore dilute the adsorbed ethanol, if it is removed from the adsorbent in the presence of the residual beer such as, for example, by blowing heated air through the bed or column. The water of the residual liquor will evaporate with the ethanol, and on condensation the recovered ethanol will be diluted by the water. This problem is particularly acute where it is desired to produce substantially anhydrous ethanol for blending with gasoline to produce gasohol, but it is a factor of significance whenever a relatively high ethanol concentration is desired, such as a concentration greater than 80% by weight ethanol.

During the experimental work leading to the present invention, it was discovered that the residual dilute aqueous solution of ethanol can be efficiently removed from the bed of adsorbent by passing highly concentrated ethanol through the bed, such as ethanol of the desired final concentration from the process. It was discovered that the residual aqueous solution can be displaced in this manner with substantially no intermixing of the concentrated ethanol displacing fluid with the aqueous solution being removed. Although ethanol and water are highly miscible, under substantially laminar flow conditions very little intermixing occurs at the interface between the concentrated ethanol and the dilute aqueous solution being displaced. This makes it possible to operate this part of the process with little loss of the concentrated ethanol, permitting it to be used repeatedly as the displacing fluid recycled for further adsorption treatment with the fermentation beer.

Since silicalite tends to retain adsorbed air and other gases, the silicalite tends to liberate gas as the ethanol is adsorbed from an aqueous solution. It appears that the ethanol is displacing the adsorbed air or other gas, causing the gas to be liberated into the beer as it is passed through the column. This creates operational problems. It has been found that this problem can be alleviated by pre-wetting of the column, for example, by flowing water through the column to substantially remove the adsorbed gas. Since the success of this procedure depends to a considerable extent on the solubility of the gas in the water, it is preferred to exclude gases from the silicalite bed which have very low solubility in water, although the bed can be operated by using air as the carrier gas for removal of the adsorbed ethanol, thereby leaving adsorbed nitrogen, oxygen, and other air gases in the column.

In a preferred embodiment of the present invention, the ethanol is removed from the silicalite bed by passing carbon dioxide gas through the bed. It has been found that carbon dioxide effectively acts as a carrier gas for the ethanol, which is vaporized and travels with the carbon dioxide. Further, at the conclusion of the desorption, carbon dioxide retained by the silicalite can be easily removed therefrom by passing water through the bed, since carbon dioxide has a high solubility in water. Thus, the problems associated with undue gassing of the bed during the next adsorption cycle are avoided. The use of carbon dioxide as the desorption carrier gas has the further advantage that it minimizes fire and explosion hazards from the ethanol.

DETAILED DESCRIPTION

Figure 1:
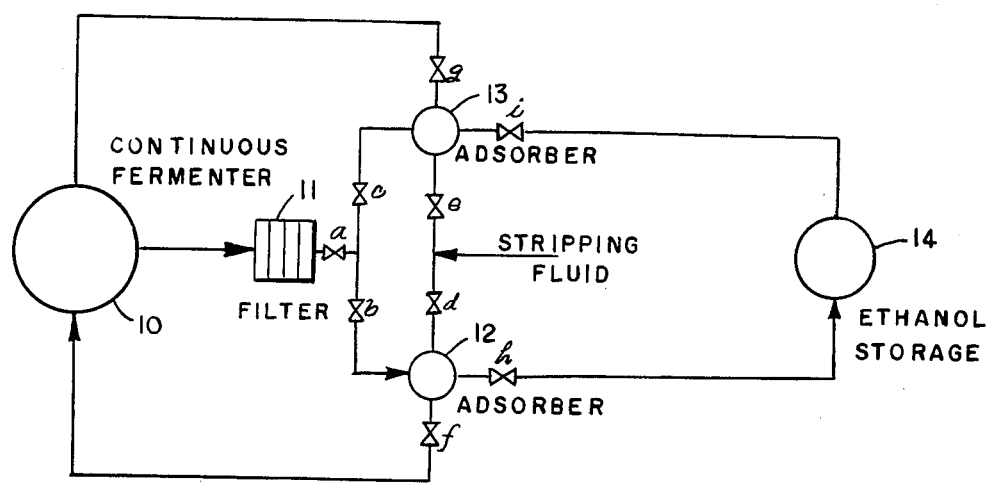

The adsorbent to be used in practicing the present invention is a crystalline silica polymorph such as the selective adsorbent described in U.S. Pat. No. 4,061,724. An adsorbent prepared in accordance with the disclosure of this patent is available commercially from the Linde Division of Union Carbide Corporation, Tarrytown, N.Y. It is sold under the generic name silicalite. An alternative adsorbent of the same general kind is described in U.S. Pat. No. 4,073,865. It should be understood that this invention is not directed to a specific adsorbent, although silicalite is preferred for the commercial practice of this invention.

In general, the process of the present invention can be applied to any aqueous solution of ethanol from which it is desired to remove and concentrate the ethanol. In its preferred applications, the concentration of ethanol in the process feed will be relatively dilute, such as an ethanol concentration within the range from 1 to 15% by weight. For example, ethanol fermentation beers can be readily produced containing from 6 to 10% ethanol. After filtration to remove solids, such fermentation beers are ready for treatment according to the present process. However, in some embodiments, if desired, the aqeous ethanol may be preconcentrated, such as by distillation. For example, such preconcentration may be desirable where the ethanol fermentations are carried out in relatively small plants at different locations, and it is desired to ship the product of these plants to a central plant for further concentration of the ethanol. In general, therefore, the process of the present invention is applicable to the treatment of aqueous ethanol solutions containing from as little as 1% ethanol up to as much as 70% ethanol by weight, although, usually, the feed stock being processed will contain substantially less than 70% ethanol.

In carrying out the process, the silicalite or other suitable crystalline silica polymorph adsorbent is prepared in the form of granules which can be employed in a bed, such as a granular bed contained within a column arranged for the passage of liquids and/or gases therethrough. The feed stock being processed is pumped through the bed until the silicalite becomes loaded with the adsorbent, as determined by monitoring the ethanol concentration of the spent feed stock passing out of the bed. The adsorption temperatures are not highly critical, and, in general, the adsorption can be advantageously carried out at temperatures within the range from about 35° to 40° C. Usually, therefore, it will not be necessary to apply very much heating or cooling to the feed stock being processed before it is passed through the adsorption column.

After the silicalite adsorbent has become loaded with the ethanol, the passing of the feed through the bed is discontinued. At this point, the bed and the column containing the bed contain residual amounts of the dilute aqueous ethanol feed, such as the fermentation beer. This residual liquid is displaced in accordance with the process of the present invention before removal of the ethanol from the adsorbent. Preferably, the residual feed is displaced from the adsorbent bed by the use of a displacer liquid comprising concentrated aqueous ethanol, such as ethanol having a concentration at least as high as the desired final product. For example, where a final product is being produced containing 80% or more ethanol by weight, the displacer fluid should comprise at least 80% ethanol. In a preferred embodiment, for producing a highly concentrated ethanol product, such as substantially anhydrous ethanol, the ethanol concentration of the displacing liquid should be at least 95% by weight, and for optimum results it should be at least 98% by weight ethanol.

The displacer liquid is passed into and through the bed in a single direction. A downflow direction is preferred but upflow can also be used. By maintaining essentially nonturbulent flow conditions, the advancing front of the concentrated ethanol will progressively displace the dilute aqueous solution in a plunger-type action with relatively little intermixing occurring at the interface. After substantially all of the dilute ethanol feed has been displaced from the bed, the bed will then contain the adsorbed ethanol together with the concentrated liquid ethanol which has been used as the displacer liquid. The column is then ready for removal of the ethanol.

Ethanol removal can be carried out in a variety of ways, using either a liquid or gas removal medium or carrier. For example, air may be passed through the bed to evaporate contents of the bed, including the adsorbed ethanol and the concentrated ethanol from the displacing liquid. The evaporated ethanol may be readily recovered by condensation thereof to produce the ethanol product at high concentration. In one embodiment, however, the preferred carrier gas is carbon dioxide. Further, the carbon dioxide or other carrier gas may be heated to promote the evaporation of the ethanol within the column. For example, temperatures ranging from about 40° to 78° C. can be used.

The carbon dioxide carrier does not need to be pure carbon dioxide. For example, the off-gas from the alcohol fermenters can be used. This gas will be composed essentially of carbon dioxide. However, where desired, pure carbon dioxide can be used, and may be recovered and recycled for further desorption after removal of the condensables therefrom (ethanol and water).

The process of this invention is further illustrated and shown in representative embodiments in the accompanying drawings.

REFERENCE TO DRAWINGS

Figure 2:
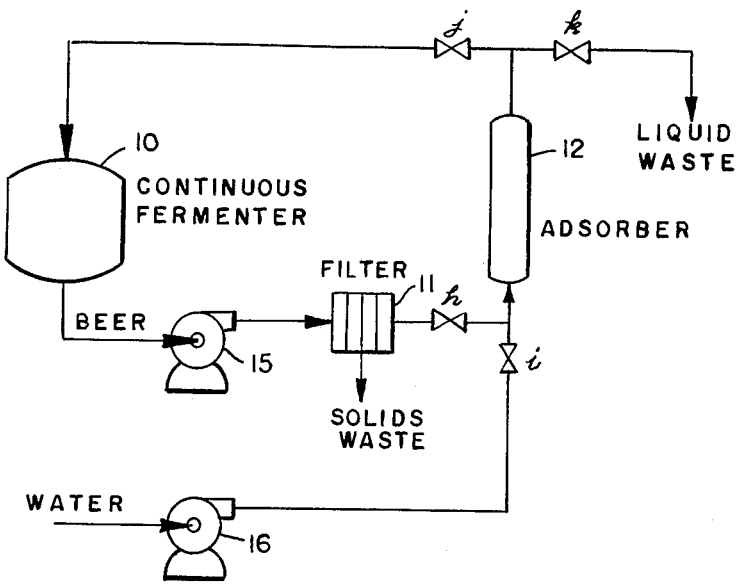
Figure 3:
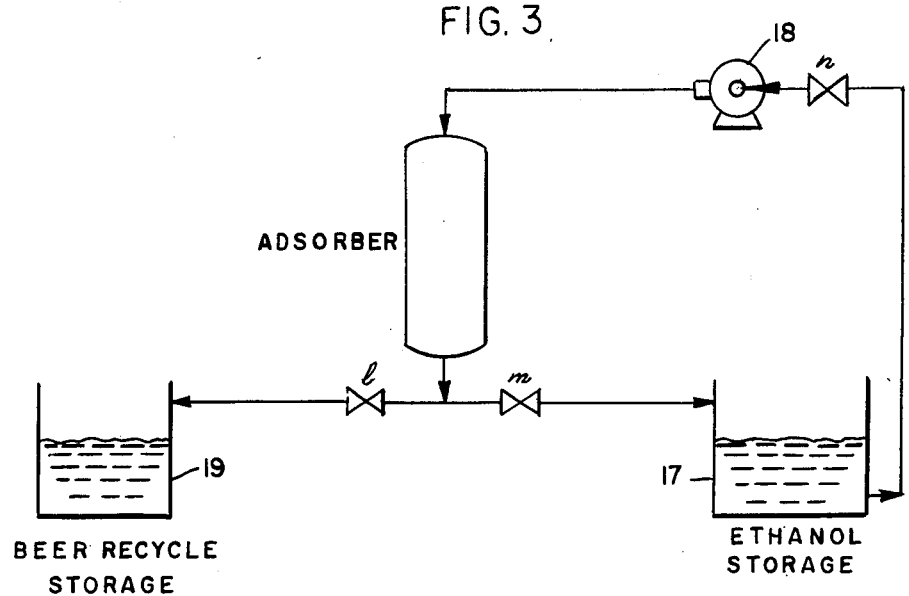
Figure 4:
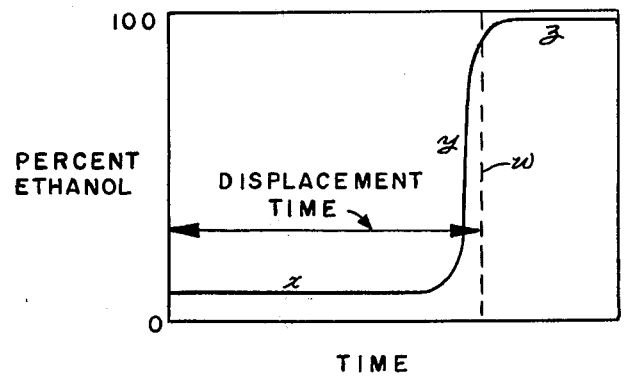
Figure 5:
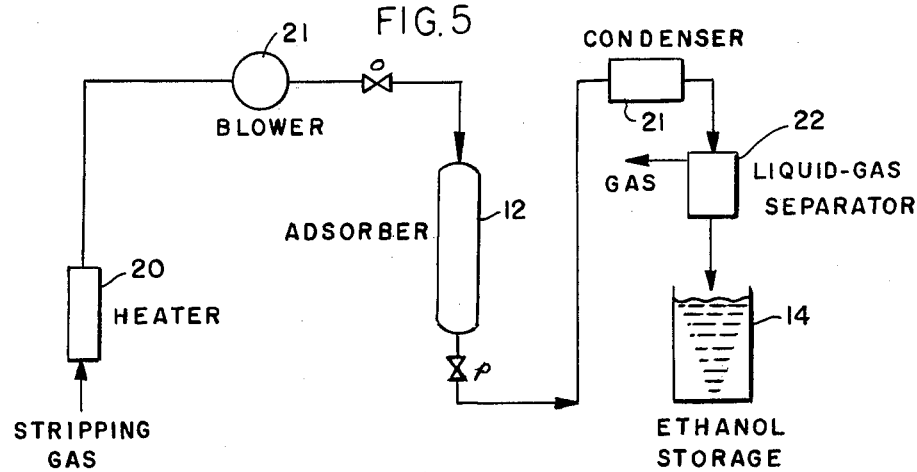

The drawings of this application comprise FIGS. 1 to 5. These figures are as follows:

FIG. 1 is an overall view of a diagrammatic flow sheet for carrying out the process of the present invention using a continuous fermenter and two alternate adsorbers;

FIG. 2 may be referred to for further illustration of the step of loading the resin with the ethanol, as well as to the step for wetting or rewetting the adsorbent prior to its use or continued use as an adsorbent;

FIG. 3 may be referred to for further illustration of the step of displacing the residual fermentation beer from the adsorbent prior to removal of the ethanol therefrom;

FIG. 4 is a graph illustrating the displacement action of the concentrated ethanol displacing fluid, as used in the step of FIG. 3; and FIG. 5 may be referred to for further illustration of the stripping or displacement step in which the ethanol is removed from the adsorbent.

Referring first to FIG. 1, there is schematically represented an operational system in which a dilute ethanol fermentation beer is produced in a continuous fermenter 10 and passed therefrom through a filter 11, and then selectively through either adsorber 12 or 13. With valves a, b open the flow is through adsorber 12 while with valve b closed and valve c open, the flow is through adsorber 13. For continuous operation, depending on the adsorber in use, the valve f or g will be open for return of the spent beer to the fermenter, since the spent beer will contain unused carbon source and nutrients which can be used for the fermentation. It will be understood that additional feed stock will be supplied to the fermenter, such as cornstarch, as required for the fermentation operation. During the adsorption of the ethanol on the silicalite adsorbent in either columns 12 or 13, the valves h and i will be closed, as well as the valves d and e. After the loading of one of the adsorber has been completed, a stripping fluid may be selectively passed to the loaded adsorber by opening the valve d, or the valve e, and passing the stripping fluid therethrough, the stripping fluid and desorbed ethanol passing through open valve h or valve e to the ethanol storage at 14. It will be understood that this flow sheet is oversimplified, and that reference must be had to the flow sheets of FIGS. 2, 3, and 5 for more complete details on the processing steps.

FIG. 2 may be referred to with respect to the step of loading the adsorber. If desired, prior to the beginning of the adsorption, with valves h and j closed, water may be passed by means of pump 16 through open valve i and the adsorber 12, passing out through open valve k to a liquid waste disposal, as indicated. After the column has been re-wet and degassed, valves i and k will be closed, and valves h and j opened. The fermentation beer is then passed from fermenter 10 by means of pump 15 through filter 11 and open valve h to the adsorber 12. The ethanol is adsorbed by the silicalite bed within adsorber 12, and the spent fermentation beer is returned to fermenter 10 through open valve j. It will be understood that a batch fermenter can also be used. Further, where a continuous fermenter is employed, the use of at least two alternate adsorbers, such as adsorbers 12 and 13 will permit continuous processing of the fermentation beer. Therefore, it should be understood that a similar system to the one shown in FIG. 2. will also be used for the other fermenter 13.

FIG. 3 illustrates the displacement step in which the residual fermentation beer is displaced from the adsorber 12 and the silicalite bed therein. After completion of the loading of the adsorber such fermentation beer as can be removed by gravity is drained from the adsorber, being returned through upon valve 1 to beer storage at 19. Thereafter, concentrated aqueous ethanol is passed from storage 17 by means of pump 18 through open valve n into and through adsorber 12. Downflow, as shown, is preferred but upflow can be used. During the initial part of the displacement, valve m on the return line to ethanol storage at 17 is closed; valve 1 is open so that the initial portion of the fluid displaced passes to a beer recycle storage tank 19. This operation can be better understood by reference to FIG. 4. This comprises a graph showing the plot of ethanol concentration versus time during the displacement step. The initial horizontal portion of the displacement curve "x" represents the percent ethanol concentration of the residual fermentation beer, such as a concentration of 6 to 10% by weight. After the residual beer has been substantially completely displaced, the concentration of the effluent increases rapidly, as represented by the substantially vertical portion of the curve "y". The concentration of the effluent rises rapidly until it corresponds to the concentration of the ethanol in the displacer fluid, such as a concentration of 90–95% ethanol. The upper horizontal portion of the curve "z" represents this concentration. In terms of practical operation, the valve m is kept closed and valve 1 open for the displacement time as represented by the arrow line extending to the time "w". At that point, the valve m is opened and the valve 1 closed, thereby returning the concentrated ethanol to storage at 17. The sharp transition between the graph portions "x" and "z" indicates that there is substantially no intermixing between the concentrated ethanol and the dilute beer being displaced. This permits the ethanol to be returned to storage at 17 and reused, while the beer can be collected at 19 and recycled to the adsorber during the next adsorption operation. Slightly more intermixing may occur if the displacing ethanol is passed upwardly through the column, since ethanol has a lower specific gravity than the beer.

FIG. 5 represents the stripping or desorption operation. A stripping gas may be passed through a preheater 20 and passed by means of blower 21 through open valve o into the top of adsorber 12 where it is passed downwardly through the bed of silicalite containing the adsorbed ethanol. The stripping gas will evaporate the ethanol. The carrier gas and the evaporated ethanol can then be passed through open valve p to a condenser 21 in which the ethanol is liquified. The gas and condensate can then be passed to a liquid-gas separator 22 from which the stripping gas is discharged, and the liquified ethanol passed to ethanol storage at 14. In a preferred embodiment, the stripping gas is composed primarily of carbon dioxide, such as the fermentation off-gas from the continuous fermenter 10 (FIGS. 1 and 2). This carbon dioxide gas can be dried and used as the stripping gas, being pre-heated and passed through the adsorber as previously described. If desired, the carbon dioxide gas from the liquid-gas separator 22 can be reused in the process. As described above, residual carbon dioxide within adsorber 12 can be readily removed during the pre-wetting of the adsorber. For example, as shown in FIG. 2, after the completion of the desorption water can be passed through adsorber 12 by means of pump 16 with valve d open until substantially all of the carbon dioxide has been removed therefrom. The carbon dioxide containing water will be passed through open valve j to disposal as liquid waste. The column will then be ready for use in another adsorption cycle.

Further details concerning a preferred embodiment of the present invention are set out in the following example.

OPERATIONAL EXAMPLE

This example illustrates preferred conditions of operation as presently known. A fermentation beer at about 35 to 40° C. containing about 6 percent ethanol by volume that has been produced by fermentation of a corn mash is filtered continuously on a pressure leaf filter to remove the bulk of the particulate matter. The clarified beer flows from the filter into the bottom of an adsorption column containing ⅛ inch diameter by ⅛ inch long pellets of silicalite. As the fermentation beer flows upward through the bed of adsorbent, the ethanol is adsorbed by the silicalite and the fermentation beer depleted of ethanol is returned to the fermenter. Fermentation beer is applied to the adsorber at the rate of about 0.2 gpm/ft$^2$ until about 2.5 bed volumes of fermentation beer containing 6 percent ethanol have been processed. This application of fermentation beer represents a loading of about 1.1 gal of ethanol per cu ft of silicalite which is near the adsorption capacity of the silicalite.

The bed of adsorbent which is now saturated with ethanol is drained to remove residual fermentation beer which is filling the void spaces between the adsorbent pellets as well as the space in the column over the adsorbent and the connecting pipes. Carbon dioxide, the stripping gas that will be used in regenerating the adsorbent is admitted into the column to fill the space that was previously occupied by the fermentation beer. Product ethanol at about 98 percent by volume is then pumped into the top of the column to displace by downflow the residual fermentation beer that was not removed by the gravity drainage. The product ethanol is at ambient temperatures and is not heated to match the temperature of the adsorption column and the fermentation beer. The amount of residual fermentation beer that will remain in the bed will amount to about 5% of the void space between the pellets of adsorbent or about 0.15 gal per cu ft of adsorption bed. The intermixing of residual fermentation beer with the product ethanol used for displacement is minimal so that when about this volume of liquid has been displaced into the fermentation beer recycle storage tank, additional product ethanol pumped through the column can be returned to the ethanol storage tank. A refactometer can be used as a detector for controlling the diversion of flow from the fermentation beer recycle storage tank to the ethanol storage tank because the concentration of ethanol will jump abruptly from 6% to 98% when displacement has been completed.

After the displacement step has been completed, the ethanol filling the bed can be displaced with carbon dioxide gas. The $CO_2$ is preheated to about 70° C., and is moved downward through the adsorption bed by means of a blower. Initially, ethanol filling the voids of the adsorption bed is simply displaced through the condenser and liquid-gas separator and into the ethanol storage tank. As stripping continues, the remaining ethanol saturating the adsorbent pellets is evaporated by hot carbon dioxide. The ethanol vapor is condensed by the condenser and is subsequently separated from the carbon dioxide in the liquid-gas separator. The carbon dioxide is recycled to the heater to be reused in the stripping cycle. Recycling the carbon dioxide limits the amount of water that is introduced into the product by the stripping gas. Alternately, the carbon dioxide can be put through a drying cycle to remove excess water. About 5000 bed volumes of carbon dioxide will regenerate the capacity of the adsorption bed to about 1.1 gal of ethanol per cu ft of adsorption bed. Lesser amounts of stripping gas can be used but the level of regeneration will affect the amount of capacity recovered.

After stripping, water at about 35° to 40° C. can be pumped through the adsorption bed in an upflow mode to rewet the column and to remove carbon dioxide filling the void space surrounding the adsorption pellets. Periodically, as needed the rate of water flow can be increased to a high enough rate to backwash particulate matter out of the adsorption bed and thereby keep the bed relatively free of solids deposits. The water washed through the bed becomes a liquid waste. Following the water wash, the adsorption bed is ready to process fermentation beer again.

We claim:

1. The process of concentrating ethanol from an aqueous solution thereof, comprising:
   (a) passing a relatively dilute liquid aqueous ethanol feed through a bed composed of graules of a crystalline silica polymorph capable of selectively adsorbing ethanol from an aqueous solution thereof, said feed having an ethanol concentration of less than 70% by weight.
   (b) discontinuing the passing of said feed through said bed when said granules have become loaded with adsorbed ethanol, said bed containing residual dilute aqueous ethanol feed;
   (c) passing a displacer liquid through said bed to displace said residual feed without displacing the adsorbed ethanol, said displacer liquid comprising aqueous ethanol containing at least 80% ethanol by weight;
   (d) continuing said passing of said displacer liquid through said bed until substantially all of said dilute ethanol feed has been displaced from said bed so that it contains said adsorbed ethanol together with said displacer liquid; and
   (e) thereafter removing said adsorbed ethanol from said bed together with at least a portion of displacer liquid and obtaining a concentrate product consisting of an admixture thereof which has an ethanol concentration of at least 80% by weight.

2. The method of claim 1 in which said silica polymorph is silicalite.

3. The method of claim 1 or claim 2 in which said ethanol feed has an ethanol concentration of from 1 to 15% by weight.

4. The method of claim 1 or claim 2 in which both said displacer liquid and concentrate product have an ethanol concentration of at least 95% by weight.

5. The process of concentrating ethanol from a dilute aqueous solution thereof, comprising:
   (a) passing a dilute liquid aqueous ethanol feed through a column containing a bed composed of granules of silicalite, said feed having an ethanol concentration of from 1 to 15% by weight;
   (b) discontinuing the passing of said feed through said bed when said granules have become loaded with adsorbed ethanol, said column and said bed therein containing residual dilute aqueous ethanol feed;
   (c) passing a displacer liquid through said column to displace said residual feed without displacing the adsorbed ethanol in said bed, said displacer liquid comprising aqueous ethanol having an ethanol concentration of at least 95% by weight;
   (d) continuing said passing of said displacer liquid through said column until substantially all of said dilute ethanol feed has been displaced from said bed and said column so that said bed contains absorbed ethanol together with said displacer liquid; and
   (e) thereafter removing said adsorbed ethanol from said bed together with at least a portion of said displacer liquid and obtaining a concentrate product consisting of an admixture thereof which has an ethanol concentration of at least 95% by weight.

6. The process of claim 5 in which both said displacer liquid and concentrate product have an ethanol concentration of at least 98% by weight.

7. The process of claim 5 or claim 6 in which said displacer liquid is passed through said bed with substantially no intermixing thereof with said residual feed.

8. The method of claim 1 or claim 5 in which said adsorbed ethanol is removed by passing a carrier gas through said bed which is composed essentially of carbon dioxide.

9. The method of claim 1 or claim 5 in which water is passed through said bed following the removal of said ethanol therefrom to prepare said bed for further adsorption of ethanol.

10. The method of claim 1 or claim 5 in which said adsorbed ethanol is removed by passing a carrier gas through said bed composed essentially of carbon dioxide, and thereafter water is passed through said bed to remove retained carbon dioxide therefrom in preparing said bed for further adsorption of ethanol.

11. The process of claim 1 or claim 5 in which said displacer liquid is passed downwardly through said bed.

* * * * *